United States Patent
Matsuoka et al.

(10) Patent No.: US 6,590,129 B2
(45) Date of Patent: *Jul. 8, 2003

(54) METHOD FOR PREPARING AROMATIC CARBOXYLIC ACIDS, AROMATIC ALDEHYDES, AND AROMATIC ALCOHOLS

(75) Inventors: Shotaro Matsuoka, Nagoya (JP); Masaaki Suematsu, Nissin (JP); Akira Kitamura, Nagoya (JP)

(73) Assignee: Toray Industries, Inc. (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/812,135

(22) Filed: Mar. 19, 2001

(65) Prior Publication Data

US 2001/0016667 A1 Aug. 23, 2001

Related U.S. Application Data

(62) Division of application No. 08/855,072, filed on May 13, 1997, now Pat. No. 6,242,643.

(30) Foreign Application Priority Data

May 17, 1996 (JP) .............................. 8-123147
May 17, 1996 (JP) .............................. 8-123148
May 17, 1996 (JP) .............................. 8-123149

(51) Int. Cl.$^7$ ..................... C07C 27/10; C07C 27/12; C07C 45/41
(52) U.S. Cl. ................ 568/815; 568/426; 568/431
(58) Field of Search ................. 568/431, 810, 568/815, 438, 426; 562/412, 418, 421, 422

(56) References Cited

U.S. PATENT DOCUMENTS

| | | | | |
|---|---|---|---|---|
| 1,815,985 A | * | 7/1931 | Pansegrau | |
| 2,245,528 A | | 6/1941 | Loder | 260/524 |
| 3,387,036 A | * | 6/1968 | Bonnart et al. | 260/599 |
| 3,607,920 A | | 9/1971 | Clark | 260/524 |
| 3,658,875 A | * | 4/1972 | Brunie et al. | 260/465 R |
| 3,679,740 A | | 7/1972 | Massie | 260/524 |
| 3,714,263 A | | 1/1973 | Cyba | 260/592 |
| 3,751,480 A | * | 8/1973 | Brunie et al. | 260/599 |
| 3,855,305 A | * | 12/1974 | Gay et al. | |
| 3,865,870 A | | 2/1975 | Cronauer et al. | 260/524 |
| 5,144,066 A | | 9/1992 | Saitou et al. | |
| 6,242,643 B1 | * | 6/2001 | Matsuoka et al. | |

FOREIGN PATENT DOCUMENTS

| | | |
|---|---|---|
| DE | 2 258 503 | 11/1971 |
| FR | 2 379 500 | 9/1978 |
| GB | 970 492 | 9/1978 |
| JP | 56 055341 | 11/1981 |
| JP | 59 053442 | 8/1984 |

OTHER PUBLICATIONS

Chemical Abstracts, vol. 108, No. 3, Cvengrosova Z et al, :Study of p-xylene reaction with cobalt-bromine-pyridine catalyst. Part II. Reaction in aqueous system, p. 552.
Steinmetz, J. Catal., vol. 100, pp. 549–551, 1986.
Hronec, Collect. Czech. Chem. Commun., vol. 41, pp. 350–359, 1976.
Hronec, Collect. Czech. Chem. Commun., vol. 42, pp. 1851–1858 1977.
Hronec, Collect. Czech. Chem. Commun., vol. 42, pp. 3392–3401 1977.
Hronec, Collect. Czech. Chem. Commun., vol. 43, pp. 728–733, 1978.
Hronec, Collect. Czech. Chem. Commun., vol. 45, pp. 880–887, 1980.

* cited by examiner

*Primary Examiner*—Brian Davis
(74) *Attorney, Agent, or Firm*—Piper Rudnick LLP

(57) ABSTRACT

An aromatic carboxylic acid, aromatic aldehyde, and aromatic alcohol are simultaneously and efficiently prepared by liquid phase oxidizing an aromatic compound represented by formula (I) with a gas containing molecular oxygen, in a presence of a catalyst comprising transition metal compound, tertiary amine and bromide compound:

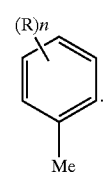

(I)

4 Claims, No Drawings

METHOD FOR PREPARING AROMATIC CARBOXYLIC ACIDS, AROMATIC ALDEHYDES, AND AROMATIC ALCOHOLS

This is a division of Ser. No. 08/855,072 filed May 13, 1997, now U.S. Pat. No. 6,242,643.

BACKGROUND OF THE INVENTION

1. Field of the Invention

The present invention concerns an efficient method for preparing aromatic carboxylic acids, aromatic aldehydes, and aromatic alcohols, wherein the aromatic carboxylic acids, aromatic aldehydes, and aromatic alcohols are compounds represented by following formulae (II), (III), and (IV);

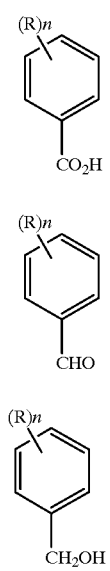

(wherein n represents any of integer 1 to 5; and substituent R represents an alkyl group, an aryl group, an aralkyl group, halogen atom, haloalkyl group, $OR^1$, $SR^1$, $SOR^1$, $SO_2 R^2$, $NO_2$, $NR^1R^2$, $CH_2OR^1$, $CH(OR^1)(OR^2)$, $C(OR^1)(OR^2)(OR^3)$, $COR^1$, or $COCOR^1$ (wherein each of $R^1$, $R^2$, and $R^3$ is selected from an alkyl group, an aryl group, and hydrogen atom); and when n takes 2 or more, R may be the same or different).

The aromatic carboxylic acids, aromatic aldehydes, and aromatic alcohols are all regarded as industrially important raw materials for pharmaceutical and agricultural products, and polymer products.

2. Prior Art

A reaction for producing the aromatic carboxylic acids from aromatic compounds having methyl group, such as chlorotoluene, nitrotoluene, and the like, by oxidation, such as air oxidation, is well known technique. Further, it is also well known that in said reaction an industrially important byproduct, such as aromatic aldehyde, aromatic alcohol, and etc., is produced.

In the oxidizing reaction, to effectively produce the aimed aromatic carboxylic acid by suppressing forming various intermediate oxidizing products, several approaches have been tried so far. For instances, a method for producing p-toluic acid by oxidation with a gas containing oxygen, in the presence of specific shaped catalyst of cobalt oxide (British Patent 1,005,315), a method for producing benzoic acid derivatives by liquid phase oxidation of toluene derivatives with a gas containing oxygen in the presence of phase transfer catalyst composed of quaternary onium salt and transition metal salt, and together with a small amount of polar solvent, which is capable of dissolving said catalyst (JP-A-1-2287054, "JP-A" used herein means unexamined Japanese Patent Publication), and the like, may be exemplified.

On the other hand, it is well known that aromatic carboxylic acid may be obtained by distilling, sedimenting with acid, or crystallizing reacting solution, or that aromatic aldehyde and aromatic alcohol may also be obtained by directly distilling the reacting solution, or by extracting effective component from the reacting solution using extracting solution, followed by rectifying thereof. (JP-B-48-23430, "JP-B" used herein means examined Japanese Patent Publication, JP-A-53-82734, JP-A-54-79244, JP-B-62-2576, JP-B-62-30974, JP-B-62-30975, JP-A-2-73038, JP-B-4-3370, JP-B-7-116096, and International Patent Publication 95-20560, and etc.).

Of the aromatic carboxylic acids, p-toluic acid may be produced by oxidizing p-xylene. As the byproduct of the reaction, p-methylbenzyl alcohol, p-tolualdehyde, p-hydroxymethylbenzoic acid, 4-carboxybenzaldehyde, terephthalic acid and the like, may be formed.

For purifying p-toluic acid produced, a physical process, such as distillation, extraction, and recrystallization, which are conventionally used, has not been applied, due to sublimable property of p-toluic acid, or readily soluble property in various solvents.

As a purifying process for p-toluic acid, a process has been known, which comprises treating at high temperature crude p-toluic acid solution in organic solvent, which is capable of selectively reacting in forming salt of the byproducts, and removing the salt, thus produced, in water extraction, and cooling the same (JP-A-54-79244). Subsequently, a washing of crystal with n-hexane is carried out to further improve purity of the p-toluic acid.

However, since an oxidizing reaction according to the conventional method is exclusively aimed at efficiently producing aromatic carboxylic acid from the aromatic hydrocarbons, regardless of the fact that some of the intermediates in the oxidation process, for example, aromatic aldehyde, and aromatic alcohol, are useful as a raw material for pharmaceutical or agricultural products, the intermediates are disposed as impurities, and are not efficiently utilized.

On the other hand, an attempt for effectively isolating whole compounds from the reacting solution containing these compounds, cannot be said as being sufficiently conducted. That is, since when an aromatic carboxylic acid is to be produced, all compounds other than the aromatic carboxylic compound, which includes aromatic aldehyde, and aromatic alcohol, are considered as impurities, a purification of the aromatic carboxylic acid must be carried out.

However, the aromatic aldehyde or aromatic alcohol is reacted and decomposed, and is liable to be adversely affected in said purification thereof. The similar phenomenon appears in the process for obtaining aromatic aldehyde and aromatic alcohol. As concrete examples, it is well known that if, generally, an aldehyde and alcohol are heated under acidic condition, an acetal is formed with 1 mole of aldehyde and 2 mole of alcohol. Said reaction is the same phenomenon as those for purifying aromatic aldehyde and aromatic alcohol under distillation. By forming acetal in the distillation, an yield of the aromatic aldehyde and aromatic alcohol may be reduced, resulting in lowering yield, as well as purity. Thus, it is difficult to be capable of effectively obtaining all three kinds of the compounds according to a combination of simple unit operation.

Besides these, among the aromatic carboxylic acid, p-toluic acid causes significantly large loss of the product in washing operation, due to solubility thereof. In this connection, although p-methylbenzyl alcohol and p-tolualdehyde, which are byproducts, may form p-toluic acid by subsequent oxidation, these byproducts have never been recovered, nor utilized, so far.

SUMMARY OF THE INVENTION

An object of the present invention is to provide a method for efficiently preparing aromatic carboxylic acid, simultaneously with aromatic aldehyde and aromatic alcohol, which comprises liquid phase oxidizing an aromatic compound represented by formula (I) with a gas containing molecular oxygen, in the presence of catalyst composed of transition metal compound, tertiary amine, and bromide compound.

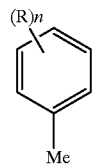

(I)

(wherein n represents any of integer 1 to 5; and substituent R represents an alkyl group, an aryl group, an aralkyl group, halogen atom, haloalkyl group, $OR^1$, $SR^1$, $SOR^1$, $SO_2R^2$, $NO_2$, $NR^1R^2$, $CH_2OR^1$, $CH(OR^1)(OR^2)$, $C(OR^1)(OR^2)(OR^3)$, $COR^1$, or $COCOR^1$ (wherein each of $R^1$, $R^2$, and $R^3$ is selected from an alkyl group, an aryl group, and hydrogen atom); and when n takes 2 or more, R may be the same or different).

Another object of the present invention is to provide a method for efficiently obtaining aromatic aldehyde by acid depositing, or crystal precipitating treatment for reacting solution, which is obtained by the oxidizing the compound represented by formula (I), and simultaneously obtaining aromatic aldehyde and aromatic alcohol from filtrate by treatment, such as distillation.

Still another object of the present invention is to provide a method for attaining preferable result due to a removal of acid, which Will become as a catalyst in acetal forming reaction, by adding base into a mixture solution containing aromatic aldehyde and aromatic alcohol to be distilled, in order to suppress producing aromatic aldehyde and aromatic alcohol in distillation step.

Further object of the present invention is to provide a method for efficiently preparing aromatic carboxylic acid of high purity, which comprises purifying crude aromatic hydrocarbons, obtained by oxidizing aromatic hydrocarbons having at least one methyl groups, by washing with raw aromatic hydrocarbons, and simultaneously using in a recycled manner, as a raw material, from which solution and crude aromatic carboxylic acid are removed by washing step.

Still further object of the present invention is to provide a method for preparing by efficiently obtaining aromatic carboxylic acid, aromatic aldehyde, and aromatic alcohol, simultaneously.

DETAILED DESCRIPTION OF THE INVENTION

The present invention is explained concretely, in more detailed below.

In the oxidizing reaction of the present invention, at least one of the aromatic hydrocarbons represented by following formula (I) is used as a raw material.

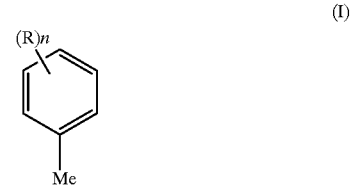

(I)

(wherein n, R, $R^1$, $R^2$, and $R^3$ are as defined above)

Furthermore, raw materials comprising at least one of aromatic hydrocarbons, or oxidizing products thereof, wherein substituent R in the formula (I) represents any of an alkyl group, an aryl group, or an aralkyl group, are preferably used.

For example, xylene, methylbenzaldehyde, and methylbenzyl alcohol are preferably used as a raw material.

The reaction is characterized by liquid phase oxidation with a gas containing molecular oxygen, in the presence of catalyst comprising transition metal compound, tertiary amine, and bromide compound, and is to produce aromatic carboxylic acid, aromatic aldehyde, and aromatic alcohol, simultaneously.

An amount of the transition metal compound to be used is preferably less than 0.2 wt %, calculated as transition metal, with respect to the raw material. If the amount is over thereof, a load in operation and coast for separating the transition metal compound from the raw material may be increased.

The transition metal used as the transition metal compound is preferably selected from 5 to 10 groups in the long-form Periodic Table, and several elements may be used in combination to further improve catalytic activity.

At least one of manganese, tungsten, molybdenum, chromium, vanadium, cobalt, and cerium are preferable, and cobalt is the most preferable.

No specific problem may be caused in using any of the transition metal compound, if the compound contains the transition metals discussed above. However, in consideration of solubility in reaction system, or availability in commercial market, chlorides, bromides, acetates, and sulfates thereof are preferred.

Example of the preferable transition metal compounds includes cobalt chloride, cobalt bromide, and cobalt acetate.

A weight ratio of the transition metal-compound to tertiary amine is preferably within a range of 1:0.1 to 1:100, more preferably 1:1 to 1:30, further more preferably 1:5 to 1:20. Since even if an excess amount of the tertiary amine may be used, no remarkable advantage may be attained, the use thereof in an excess amount should be avoided.

A kind of the tertiary amine to be used has no specific limit, however, a use of aromatic amine such as pyridine, picoline, lutidine; and xynoline, and aliphatic amine, such as tributyl amine, and triethyl amine, are preferred.

A weight ratio of the transition metal compound to the bromide compound is preferably within a range of 1:0.1 to 1:100, more preferably 1:1 to 1:30, further more preferably 1:5 to 1:20. A use of the bromide compound in large amount, is not preferable due to causing corrosion of apparatus.

An example of the bromide compounds includes inorganic bromide compound, such as hydrogen bromide, alkali metal bromide, and ammonium bromide, and organic bromide compound, such as tetrabromoethane, bromoacetate, and bromobenzyl, as available.

According to the present invention, a small amount of water may be added into a charged mixture containing raw material and catalyst. The amount thereof is 0.01 to 20 wt % with respect to the amount of the raw material, more preferably 1.0 to 10 wt %. By the addition of the water makes selectivity of the aromatic alcohol improved.

The oxidation reaction of the present invention may be carried out at a temperature of 100 to 250° C., preferably 140 to 200° C. With higher temperature a side reaction may be caused, whereas with lower temperature a reaction rate may be remarkably lowered.

As for a gas containing molecular oxygen, although pure oxygen or industrial exhaust gas may be used, in the industrial use common air or a mixture of air and industrial exhaust gas are suitably available.

A reaction pressure is preferably within a range of 0.1 to 6 MPa, preferably 0.5 to 2 MPa, and an oxygen content in a waste gas from the reactor is preferably controlled so as to be below explosion limit in concentration.

The reaction may be carried out in the presence of a solvent, wherein the solvent is preferably inactive under the oxidizing reaction.

A reactor to be used in the present invention, is preferably of a forced stirring type, rather than simple bubbling tower type. That is, in order to accelerate dissolving the gas containing molecular oxygen into the reaction mixture, and smoothly contact reactants each other, in the reactor, it is preferable to use a reactor, which provides with many gas blowing nozzles at lower part thereof, and is capable of operating in a forced stirring with revolving stirring vane, or circulating pump provided at outside thereof.

At the upper part of the reactor, a reflux condenser is provided so that the waste gas may be exhausted through said reflux condenser, and the solvent, raw material, etc. which are accompanied with the waste gas are condensed and recycled to the reactor.

As one of the most conventional example proceedings in the reaction steps, a process, which comprises heating the aromatic hydrocarbons, i.e., raw material, in the presence of the catalyst, comprising transition metal compound, tertiary amine, and bromide compound, and introducing gas containing molecular oxygen gas, may be shown. When the oxidation reaction is carried out as far as consuming the raw material to 10 to 70% (conversion of 10 to 70%), generally takes about 0.5 to 10 hours, the aromatic carboxylic acid, aromatic aldehyde, which is an intermediate, and aromatic alcohol are formed in selectivity of 20 to 70%, 10 to 40%, and 5 to 30%, respectively, and reaction product solution, containing small amount of the byproducts, etc., may be obtained.

In separation and purification steps for the aromatic carboxylic acid, aromatic aldehyde, and aromatic alcohol, according to the present invention, a reaction solution obtained by oxidizing the aromatic compounds is used.

As for the aromatic compound used in the present invention as a raw material, any of the compounds represented by formula (I) may be used. A concrete example thereof includes xylene, ethyl toluene, cumene, butyl toluene, trimethyl benzene, tetramethyl benzene, chlorotoluene, bromotoluene, iodotoluene, anisole, phenoxy toluene, nitrotoluene, and etc., and preferably xylene.

To obtain oxidizing reaction solution used in the present invention, other than the liquid phase reaction using a gas containing molecular oxygen, in the presence of the transition metal, such as cobalt, manganese, etc., a gas phase oxidation, or a liquid phase or gas phase oxidation using oxidizing agents, such as permanganic acid chromic acid, hydrogen peroxide, nitric acid, etc., may be used. Among these, the liquid phase oxidation reaction using a gas containing molecular oxygen is the most preferred.

The reaction solution, obtained by the above process, is separated into the aromatic carboxylic acid and residue containing aromatic aldehyde, and aromatic alcohol, by cooling or crystallizing, after condensing thereof, on demand. At the same time, the aromatic carboxylic acid further purified, may be obtained by recrystallization of the crude aromatic carboxylic acid, and the like. Or depending on the process, the aromatic carboxylic acid further purified, may be obtained by treating the reaction solution with a base to separate the salts, obtained, i.e., compounds, which is to be impurities of the aromatic carboxylic acid, aromatic aldehyde, and aromatic alcohol, followed by cooling and crystallization.

An example of the base, which may be used for treating the reacting solution, includes an aqueous solution of sodium hydroxide, potassium hydroxide, calcium hydroxide, potassium carbonate, calcium carbonate, sodium hydrogencarbonate, etc., and an aqueous solution of organic basic compounds, such as pyridine, picoline, triethylamine, tripropylamine, tributylamine, etc. These bases may be used either alone or in combination. A treating temperature has no specific limit, however, in consideration of operability or probability in causing side reaction, the temperature is preferable to be as low as possible, which is 60 to 120° C. Further, a reaction time has also no specific limit, since the reaction is for simple neutralization, however, in consideration of probability for causing the side reaction, the reaction time is not required for carrying out unnecessarily long time, and 5 to 60 minutes may be sufficient. In these connection, an amount of the base is used in 1.0 to 10.0 times mole of an amount of the impurity, preferably 3.0 to 7.0 times mole. An amount of water, which is required for dissolving the base, is also not specifically limited, however, in consideration of loss of the effective component, an amount of 0.05 to 0.3 wt % of the reaction solution may be sufficient for removing the impurity. From, the stand point for removing the impurity, a repeated treatment of the same operation is acceptable.

Depending on the process, in advance of the cooling and crystallization, an impurity dissolved in a water layer part, wherein the water is derived from byproduct in the oxidation reaction, is preferably removed previously. Under the circumstances, after adding water from outside and stirring the mixture, and removing the water phase, it is further preferable in view of surely removing the impurity. Furthermore, the water phase obtained by the above process may be available for recycling to the original oxidation reaction depending on the process, since the water phase is mainly composed of the catalyst component.

On the other hand, by distillating a filtrate after crystallization, the aromatic aldehyde, and aromatic alcohol may be obtained. At the same time, by distilling a solution obtained after removing the acid component, such as aromatic carboxylic acid, etc., contained, the aromatic aldehyde and aromatic alcohol are able to be more efficiently obtained.

As for a technical process for removing the acid component, such as aromatic carboxylic acid, etc., if an acid component shows volatility, and is capable of being removed through distilling condensation process, almost part of said component may be removed. On the other hand, if the acid component will be difficult for removing by condensation, said component may be removed by any method of repeatedly conducting condensing and crystallization, neutralizing removal with required amount of the base, absorbing removal with ion-exchange resin, or the like. In other words, depending on the nature of the acid component, various method may be considered, however, a preferable method of easily operable, and being capable of removing small amount of the acid component, is neutralizing removal with required amount of the base, regardless whether the acid component may be volatile, or not.

The base, which may be used in said removal process, includes an aqueous solution of hydroxide, such as sodium hydroxide, potassium hydroxide, calcium hydroxide, sodium carbonate, potassium carbonate, calcium carbonate, etc., and an aqueous organic basic compounds, such as pyridine, picoline, triethylamine, tripropylamine, tributylamine, etc. These bases may be used alone, or in combination. A treating temperature has no specific limit, provided that a residue may be maintained in a liquid state, and the neutralization reaction may be proceeded, however, in consideration of capability for causing side reaction, the temperature is preferably as low as possible, i.e., within a range of 60 to 120° C. A treating time has also no specific limit, a reaction is simple, however, in consideration of capability for causing side reaction, the reaction time is not required to carry out for unnecessarily long time, and is sufficient for 30 to 120 minutes. In this connection, with an amount of the base in 1.0 to 10.0 times mole with respect to amount of the acid component, preferably 1.0 to 3.0 times mole, the acid component is able to be removed.

However, according to the above process, although the almost amount of residual acid components will be removed, it is difficult to remove so small amount thereof.

According to the present invention, in order to efficiently obtain aromatic aldehyde and aromatic alcohol, since the acid component is functioned as a catalyst to form acetal, thereby lowering a purity and yield of the aromatic aldehyde and aromatic alcohol, a small amount of the acid component is required.

Accordingly, as an object for removing small amount of the acid, which will becomes a catalyst for acetal forming reaction, the base is added to a solution containing aromatic aldehyde and aromatic alcohol, which are raw materials, on distilling the solution. The acid component in the distilling raw material is captured by the base to form salt, thereby losing catalytic activity in acetal forming reaction. As for the acid, an organic acid such as carboxylic acid, etc., which is formed by the oxidizing reaction, and inorganic acid derived from a catalyst component in the oxidation reaction may be adopted.

An example of the base to be used includes an aqueous solution of hydroxides, such as sodium hydroxide, potassium hydroxide, calcium hydroxide, sodium carbonate, potassium carbonate, calcium carbonate, etc., and an aqueous organic basic compounds, such as pyridine, picoline, triethylamine, tripropylamine, tributylamine, etc. These bases may be used alone or in combination. In consideration of easy availability, problems for contaminating in the final product, sodium hydroxide is preferably used as a base in the form of aqueous solution.

An amount of the base to be added is 10 wt % or less, preferably 1 wt % or less with respect to a total amount of the aromatic aldehyde and aromatic alcohol. If the base is used in excess, an impurity will be increased due to side reaction. Further, the aromatic alcohol is liable to be decomposed by the base. If the base is not used in an amount of 1 or more mole ratio, with respect to acid component in the solution containing the aromatic aldehyde and aromatic alcohol, a suppression effect for forming acetal will be lowered.

Furthermore, a residue obtained by the above distilling operation may be recycled to be used in the original oxidation reaction, depending on the operation. It is also possible to isolate effective aromatic carboxylic acid from the solution containing acid component.

According to the present invention, the aromatic carboxylic acid in high purity is efficiently prepared by washing and purifying the crude aromatic carboxylic acid, which was obtained by oxidizing aromatic hydrocarbons having at least one methyl group, with the raw aromatic hydrocarbons, and simultaneously by using the solution, which is obtained after washing operation, and from which the crude aromatic carboxylic acid is removed, in recycled manner, as a raw material.

The aromatic hydrocarbons used in the present invention as a raw material, is aromatic hydrocarbons having at least one methyl group, and the aromatic carboxylic acid produced is a benzoic acid or those substituted with alkyl group. The examples of the raw material preferably includes xylene, more preferably p-xylene, and example of the product preferably includes toluic acid, more preferably p-toluic acid.

A use of washing p-toluic acid produced, is p-xylene which is raw material, an amount of which may be decided so as to be sufficient for washing an impurity out, which is adsorbed over the crystal surface of the p-toluic acid, and so as to not dissolve large amount of the p-toluic acid.

The filtrate after obtaining toluic acid, and the washing solution for toluic acid, are combined together to be used as a raw material for the subsequent reaction. The residual impurities remained in the combined solution, show no adverse affect on a reaction to obtain p-toluic acid.

As discussed above, by establishing the method according to the present invention, the aromatic caroxylic acid, aromatic aldehyde, and aromatic alcohol are able to be simultaneously and efficiently produced.

The present invention is further explained in more detailed, with referring to the following examples, which are not construed as limiting the scope of the present invention. Unless otherwise specified, a part, ratio and percent are by weight.

EXAMPLE 1

In 1 l autoclave of titanium, having reflux condenser and revolving vane stirrer, 500 g of p-xylene (produced by Kishida Kagaku, special grade), 0.23 g of cobalt chloride 6 hydrate (Katayama Kagaku, special grade), 0.54 g of pyridine (Kishida Kagaku, special grade), and 1.18 g of hydrobromic acid were charged, and contacted with air, blown under 1.4 MPa of reaction pressure, at 170° C. of the reaction temperature for 6 hours, at such a rate that an oxygen content in an exhaust gas may be 3% or lower, and a flow rate of the exhaust gas may be 0.6 Nl/min.

According to a result in analysis, a conversion of p-xylene in this oxidation reaction was 46.8% by gas chromatography, a selectivity of p-toluic acid by high performance liquid chromatography was 46.1%, selectivity of p-tolualdehyde, and p-methylbenzyl alcohol by gas chromatography were 12.3 %, and 8.9%, respectively.

EXAMPLE 2

A process was repeated in the same manner as of the Example 1, except for using 0.13 g of tributylamine (Kishida Kagaku, special grade) was used in place of the pyridine, at a reaction temperature of 155° C.

According to a result in analysis, a conversion of p-xylene in this oxidizing reaction was 54.0% by gas chromatography, a selectivity of p-toluic acid by high performance liquid chromatography was 57.7%, selectivity rates of p-tolualdehyde, and p-methylbenzyl alcohol by gas chromatography were 10.7 %, and 8.3%, respectively.

EXAMPLE 3

A process was repeated in the same manner as of the Example 1, except for using 0.71 g of sodium bromide (Katayama Kagaku, Special grade) in place of the hydrobromic acid.

According to a result in analysis, a conversion of p-xylene in this oxidizing reaction was 48.2% by gas chromatography, a selectivity rate of p-toluic acid by high performance liquid chromatography was 47.7%, selectivity rates of p-tolualdehyde, and p-methylbenzyl alcohol by gas chromatography were 11.8%, and 7.9%, respectively.

EXAMPLE 4

In the process of the Example 1, 15 g of water (3% with respect of raw p-xylene) was added.

According to a result in analysis, a conversion of p-xylene in this oxidation reaction was 27.3% by gas chromatography, a selectivity of p-toluic acid by high performance liquid chromatography was 39.1%, selectivity of p-tolualdehyde, and p-methylbenzyl alcohol by gas chromatography were 16.5%, and 13.6%, respectively.

EXAMPLE 5

To a pressure resistive apparatus of glass, providing with liquid inlet tube, which is capable of charging alkali solution, etc., a sampling tube, which is capable of withdrawing liquid from lower layer, and revolving vane stirrer, 524 g of the reaction mixture, which was obtained according to the same condition as of the Example 1, was charged, and a pressure was raised to 0.2 MPa.G with nitrogen gas, followed by raising a temperature to 130° C. (pressure was raised to about 0.5 MPa G). Then, 15 minutes after standing still, 4.0 g of water layer, remained in the lower layer, was drawn out through the sampling tube. After that, 71.9 g of 4.9% aqueous sodium hydroxide solution (which was 0.14 times with respect to the reacting solution; an amount of the sodium hydroxide was 4.8 times in mole with respect to total amount of terphthalate and p-carboxybenzaldehyde) was added, stirred at 110° C., for 45 minutes (the pressure was about 0.3 MPa G), and similarly, after standing still for 15 minutes, 76.4 g of water layer was drawn. Further, 74.3 g of ion-exchanged water (0.14 times with respect to the reacting solution) was charged, stirred at 110° C., for 30 minutes (the pressure was about 0.3 MPa G), and after standing still for 15 minutes, 82.6 g of the water layer was drawn. After the processes above, the reacting solution was cooled to about 30° C., filtered with suction as it is, to obtain 69.6 g of cake and 418.6 g of filtrate. As for the cake, 102.2 g of p-xylene (1.5 times with respect to the cake) was added, and after stirring at 40° C. for 30 minutes, a process for filtration under suction and drying was taken place to obtain 52.4 g of p-toluic acid in white crystal (63.4% in isolated yield with respect to the toluic acid in the reacting solution). The p-toluic acid obtained showed 98.8% in purity, and 96.1% in transmission at 460 nm.

On the other hand, the result of analysis according to the high performance liquid chromatography showed compositions, as stated below:

| | |
|---|---|
| p-Xylene | 70.2% |
| p-Toluic acid | 3.8% |
| p-Tolualdehyde | 6.6% |
| p-Methylbenzyl alcohol | 4.8% |
| Terphthalic acid | <0.1% |
| p-Carboxybenzaldehyde | <0.1% |
| p-Hydroxymethylbenzoic acid | <0.1% |
| p-Methylbenzyl toluate | <0.1% |
| Other | 10.8% |

EXAMPLES 6 AND 7

The study in the Example 1 was carried out in the same manner, except that a concentration of the sodium hydroxide was varied. The results on the crystallized p-toluic acid obtained show in Table 1 below.

TABLE 1

| | Molar Factor* of NaOH (mol/mol) | Yield (%) | p-Toluic Acid Purity | Transmission at 460 nm (%) |
|---|---|---|---|---|
| Example 6 | 3.4 | 64.2 | 98.5 | 96.8 |
| Example 7 | 5.7 | 55.3 | 98.9 | 96.6 |

Remarks:
*Shows molar ratio of NaOH with respect to total amount of terphthalate and p-carboxybenzaldehyde.

EXAMPLE 8

To 2100 g of the reaction filtrate obtained in the same condition as of the Example 1, 364.0 g of aqueous sodium hydroxide solution (sodium hydroxide was 1.5 times in mole with respect to a total amount of the p-toluic acid and p-methylbenzyl toluate) was added, stirred at 90° C. for 4 hours, and after standing still 15 minutes, the solution was separated into 1937.5 g of organic layer and 372.0 g of water layer. To said organic layer, 0.27 g of aqueous 40% NaOH solution (sodium hydroxide was 0.11% with respect to total amount of the p-tolualdehyde and p-methylbenzyl alcohol contained in the solution) was added, and distilled to obtain 82.2 g of p-tolualdehyde, and 84.8 g of p-methylbenzyl alcohol. As the result of the analysis by gas chromatography, purities of the p-tolualdehyde and p-methylbenzyl alcohol were found as 99.3% and 99.5%, respectively.

EXAMPLE 9

Xylene was added to the washing solution, which was obtained by reacting in the same condition as of the Example 1, and treating with the alkali solution in the same condition as of the Example 5, and residue obtained in the same condition as of the Example 8, so that an total amount of the p-xylene was to be 500 g, together with those contained in the washing solution, and reacted in the same condition as of the Example 1. As the result of the analysis, a conversion of p-xylene was 34.8% by gas chromatography, a selectivity of p-toluic acid by high performance liquid chromatography was 45.7%, a selectivity of p-tolualdehyde, and p-methylbenzyl alcohol by gas chromatography was 15.2%, and 12.0%, respectively. The filtrate and washing solution showed the same reactivity as in the initial reaction, even on recycle using.

What is claimed is:

1. A method for preparing at least one each of an aromatic aldehyde and an aromatic alcohol from a mixture comprising the aldehyde and the alcohol, comprising the steps of:

oxidizing the aromatic compound of formula (I);

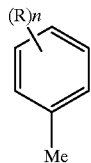

(I)

wherein n represents an of integer 1 to 5; and
substituent R represents $C_{1-18}$ alkyl group, $C_{6-18}$ aryl group, $C_{6-18}$ aralkyl group, halogen, haloalkyl group, $OR^1$, $SR^1$, $SOR^1$, $SO_2R^2$, $NO_2$, $NR^1R^2$, $CH_2OR^1$, $CH(OR^1)(OR^2)$, $C(OR^1)(OR^2)(OR^3)$, $COR^1$, or $COCOR^1$; wherein each of $R^1$, $R^2$, and $R^3$ is selected from $C_{1-18}$ alkyl group, $C_{6-18}$ aryl group, and hydrogen atom; and when n takes 2 or more, R may be the same or different;

removing intermediate aromatic carboxylic acid via addition of base; and distilling the mixture by further adding a base wherein said aromatic alcohol is produced at approximately 5–30%.

2. The method for preparing at least one each of an aromatic aldehyde and an aromatic alcohol according to claim 1, wherein the aromatic aldehyde is tolualdehyde.

3. The method for preparing at least one each of an aromatic aldehyde and an aromatic alcohol according to claim 1, wherein the aromatic alcohol is methylbenzyl alcohol.

4. The method for preparing at least one each of an aromatic aldehyde and an aromatic alcohol according to claim 1, wherein addition amount of the base is 10 wt % or less with respect to a total amount of the aromatic aldehyde and aromatic alcohol.

* * * * *